(12) United States Patent
Kashyap et al.

(10) Patent No.: US 11,273,313 B2
(45) Date of Patent: Mar. 15, 2022

(54) DYNAMIC VISUALIZATION OF NEURONAL SUB POPULATION INTERACTIONS

(71) Applicant: Boston Scientific Neuromodulation Corporation, Valencia, CA (US)

(72) Inventors: Dheerendra Kashyap, Valencia, CA (US); Natalie Brill, Sherman Oaks, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 67 days.

(21) Appl. No.: 16/852,103

(22) Filed: Apr. 17, 2020

(65) Prior Publication Data

US 2020/0330778 A1 Oct. 22, 2020

Related U.S. Application Data

(60) Provisional application No. 62/835,900, filed on Apr. 18, 2019.

(51) Int. Cl.

| | | |
|---|---|---|
| *A61N 1/372* | (2006.01) | |
| *A61N 1/378* | (2006.01) | |
| *G16H 15/00* | (2018.01) | |
| *A61N 1/36* | (2006.01) | |
| *G16H 20/30* | (2018.01) | |

(52) U.S. Cl.
CPC ..... *A61N 1/37247* (2013.01); *A61N 1/36071* (2013.01); *A61N 1/3787* (2013.01); *A61N 1/37229* (2013.01); *G16H 15/00* (2018.01); *G16H 20/30* (2018.01)

(58) Field of Classification Search
CPC ............ A61N 1/37247; G16H 20/30

USPC .......................................................... 607/46
See application file for complete search history.

(56) References Cited

U.S. PATENT DOCUMENTS

| | | |
|---|---|---|
| 7,024,247 B2 | 4/2006 | Gliner et al. |
| 7,424,322 B2 | 9/2008 | Lombardi et al. |
| 7,450,992 B1 | 11/2008 | Cameron |
| 8,255,057 B2 | 8/2012 | Fang et al. |
| 8,335,569 B2 | 12/2012 | Aghassian |
| 8,335,664 B2 | 12/2012 | Eberle |
| 8,412,345 B2 | 4/2013 | Moffitt |
| 8,498,716 B2 | 7/2013 | Chen et al. |
| 8,768,453 B2 | 7/2014 | Parramon et al. |

(Continued)

OTHER PUBLICATIONS

McIntyre, Cameron C., et al., "Modeling the Excitability of Mammalian Nerve Fibers: Influence of Afterpotentials on the Recovery Cycle," The American Physiological Society, 87, 2002, pp. 995-1006.

*Primary Examiner* — Nadia A Mahmood
(74) *Attorney, Agent, or Firm* — Lewis & Reese, PLLC

(57) ABSTRACT

Methods and systems for programming implantable stimulation devices are disclosed. The disclosed techniques may be applied to a programming interface associated with a clinician's programmer, for example. A user interface allows a user to select stimulation waveforms to be applied at a plurality of electrodes implanted in a patient and to visualize how the waveforms interact with each other and with the patient's tissue. For example, the user interface can display a representation of constructive and destructive activation interactions and can also display time-resolved spatiotemporal behavior during stimulation.

20 Claims, 11 Drawing Sheets

(56) References Cited

U.S. PATENT DOCUMENTS

| | | |
|---|---|---|
| 9,044,155 B2 | 6/2015 | Strahl |
| 9,248,274 B2 | 2/2016 | Troosters et al. |
| 9,248,279 B2 | 2/2016 | Chen et al. |
| 9,302,112 B2 | 4/2016 | Bomzin et al. |
| 9,403,013 B2 | 8/2016 | Walker et al. |
| 9,409,020 B2 | 8/2016 | Parker |
| 9,526,897 B2 | 12/2016 | Chen et al. |
| 9,731,116 B2 | 8/2017 | Chen |
| 9,792,412 B2 | 10/2017 | Moffitt et al. |
| 10,010,715 B2 | 7/2018 | Zhu et al. |
| 10,076,667 B2 | 9/2018 | Kaula et al. |
| 2009/0281594 A1 | 11/2009 | King et al. |
| 2014/0163640 A1 | 6/2014 | Edgerton et al. |
| 2015/0012067 A1* | 1/2015 | Bradley ............... A61N 1/0553 607/60 |
| 2015/0080982 A1 | 3/2015 | Funderburk |
| 2017/0056642 A1 | 3/2017 | Moffitt et al. |

\* cited by examiner

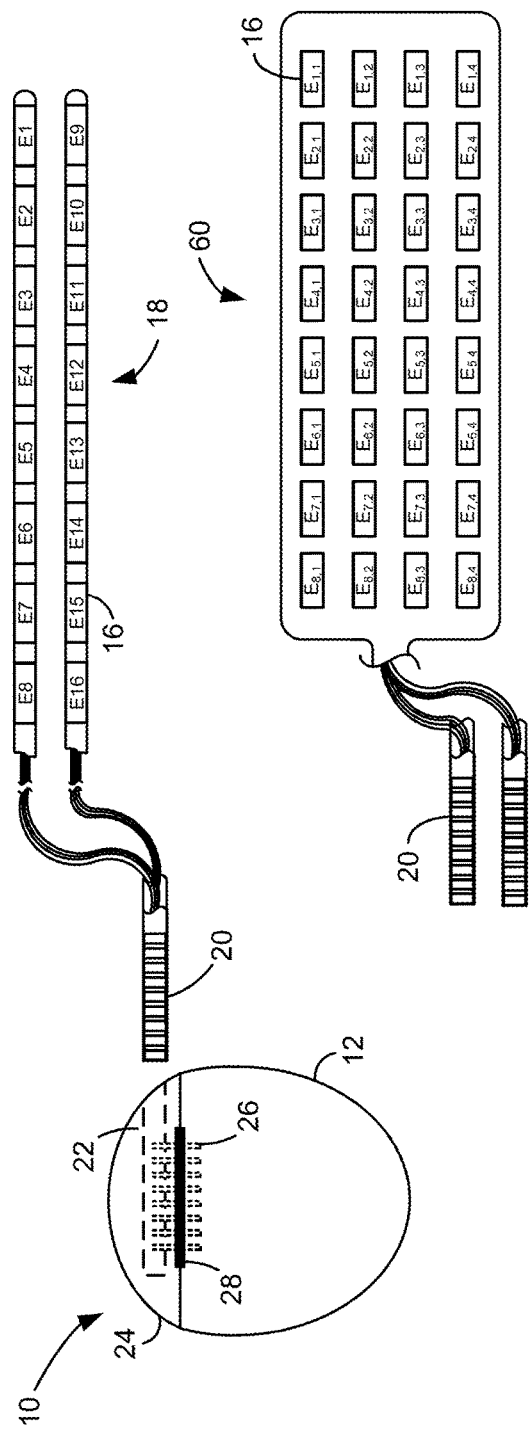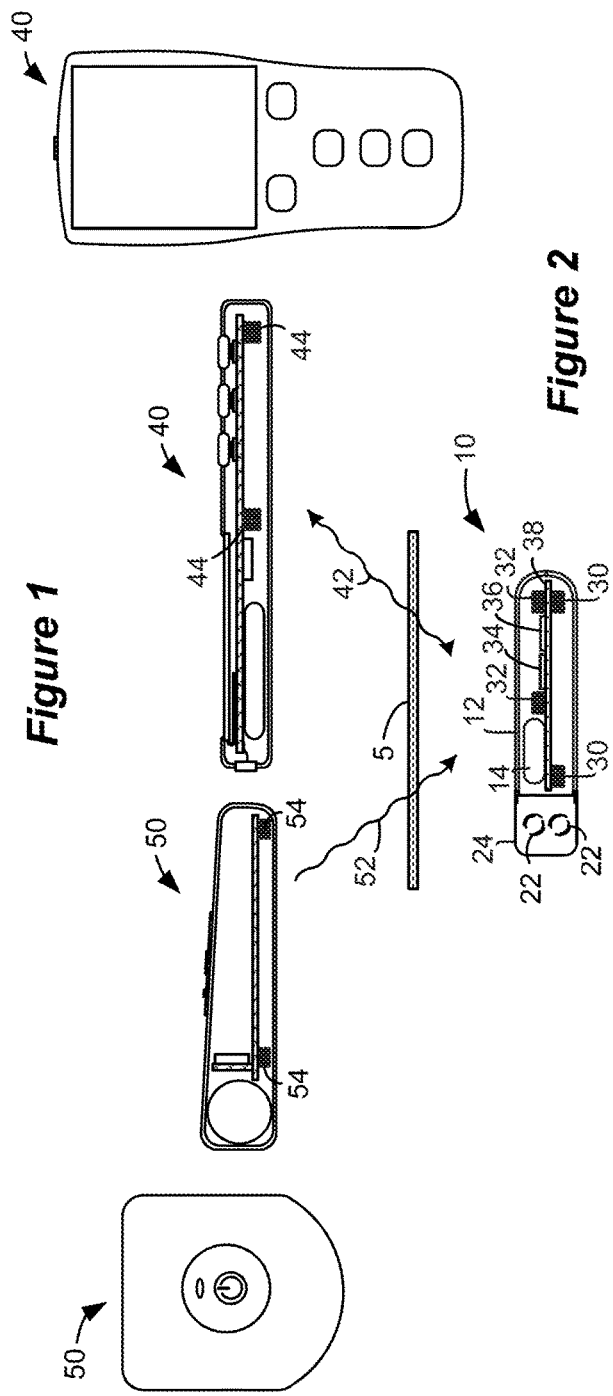
Figure 1
Figure 2

DYNAMIC VISUALIZATION OF NEURONAL SUB POPULATION INTERACTIONS

CROSS REFERENCE TO RELATED APPLICATIONS

This is a non-provisional application of U.S. Provisional Patent Application Ser. No. 62/835,900, filed Apr. 18, 2019, which is incorporated herein by reference, and to which priority is claimed.

FIELD OF THE TECHNOLOGY

Implantable stimulation devices deliver electrical stimuli to nerves and tissues for the therapy of various biological disorders. The present application is related to a technique to improve the visualization of neuronal subpopulations affected by neurostimulation.

INTRODUCTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy.

These implantable neurostimulation systems typically include one or more electrode carrying stimulation leads, which are implanted at the desired stimulation site, and a neurostimulator (e.g., an implantable pulse generator (IPG)) implanted remotely from the stimulation site, but coupled either directly to the stimulation lead(s) or indirectly to the stimulation lead(s) via a lead extension. The neurostimulation system may further comprise an external control device to remotely instruct the neurostimulator to generate electrical stimulation pulses in accordance with selected stimulation parameters.

Electrical stimulation energy may be delivered from the neurostimulator to the electrodes in the form of an electrical pulsed waveform. Thus, stimulation energy may be controllably delivered to the electrodes to stimulate neural tissue. The combination of electrodes used to deliver electrical pulses to the targeted tissue constitutes an electrode combination, with the electrodes capable of being selectively programmed to act as anodes (positive), cathodes (negative), or left off (zero). In other words, an electrode combination represents the polarity being positive, negative, or zero. Other parameters that may be controlled or varied include the amplitude, width, and rate of the electrical pulses provided through the electrode array. Each electrode combination, along with the electrical pulse parameters, can be referred to as a "stimulation parameter set."

With some neurostimulation systems, and in particular, those with independently controlled current or voltage sources, the distribution of the current to the electrodes (including the case of the neurostimulator, which may act as an electrode) may be varied such that the current is supplied via numerous different electrode configurations. In different configurations, the electrodes may provide current or voltage in different relative percentages of positive and negative current or voltage to create different electrical current distributions (i.e., fractionalized electrode combinations).

As briefly discussed above, an external control device can be used to instruct the neurostimulator to generate electrical stimulation pulses in accordance with the selected stimulation parameters. Typically, the stimulation parameters programmed into the neurostimulator can be adjusted by manipulating controls on the external control device to modify the electrical stimulation provided by the neurostimulator system to the patient. Thus, in accordance with the stimulation parameters programmed by the external control device, electrical pulses can be delivered from the neurostimulator to the stimulation electrode(s) to stimulate or activate a volume of tissue in accordance with a set of stimulation parameters and provide the desired efficacious therapy to the patient. The best stimulus parameter set will typically be one that delivers appropriate stimulation energy to the volume of tissue that is targeted for therapeutic benefit (e.g., treatment of pain), while minimizing the volume of non-target tissue that is stimulated.

However, the number of electrodes available, combined with the ability to generate a variety of complex stimulation pulses, presents a huge selection of stimulation parameter sets to the clinician or patient. For example, if the neurostimulation system to be programmed has an array of sixteen electrodes, millions of stimulation parameter sets may be available for programming into the neurostimulation system. Today, neurostimulation system may have up to thirty-two electrodes, thereby exponentially increasing the number of stimulation parameters sets available for programming.

To facilitate such selection, a patient care professional (e.g., a clinician, field engineer, sales representative, etc.) generally programs the neurostimulator through a computerized programming system. This programming system can be a self-contained hardware/software system, or can be defined predominantly by software running on a standard personal computer (PC), personal data assistant (PDA), or other computerized device. The PC or custom hardware may actively control the characteristics of the electrical stimulation generated by the neurostimulator to allow the optimum stimulation parameters to be determined based on patient feedback or other means and to subsequently program the neurostimulator with the optimum stimulation parameter set or sets, which will typically be those that stimulate all of the target tissue in order to provide the therapeutic benefit, yet minimizes the volume of non-target tissue that is stimulated. The computerized programming system may be operated by a clinician attending the patient in several scenarios.

Thus, in the application of electrical neurostimulation therapy, the goal is to identify a pertinent paradigm of stimulation that properly stimulates neural tissue. Significantly, it may sometimes be desirable to estimate or predict the stimulation effects of electrical energy applied, or to be applied, to neural tissue adjacent to electrodes based on an estimation of the membrane response (e.g. transmembrane voltage potentials) of one or more neurons induced by the actually applied or potentially applied electrical energy. For example, given a specific set of stimulation parameters, it may be desired to predict a region of stimulation within the neural tissue of a patient based on an estimation of the neuronal response.

SUMMARY

Aspects of the disclosure relate to an external device for programming an implantable medical device (IMD)

implantable in a patient, the IMD comprising an implantable pulse generator (IPG) and one or more lead wires each comprising a plurality of electrodes. According to some embodiments, the external device comprises a graphical user interface (GUI) and one or more processors. According to some embodiments, the processors are configured to cause the GUI to display a representation of the patient's anatomy. According to some embodiments, the processors are configured to receive input from a user indicating at least a first stimulation waveform to be applied at a first one or more electrodes of the plurality of electrodes and a second stimulation waveform to be applied at a second one or more electrodes of the plurality of electrodes. According to some embodiments, the processors are configured to cause the GUI to display at least one indicium of one or more interactions of the first and second stimulation waveforms with the patient's anatomy. According to some embodiments, the indicium of one or more interactions indicates a constructive activation of neural elements within the patient's anatomy by the first and second waveforms. According to some embodiments, the indicium of one or more interactions indicates a region of the patient's anatomy comprising neural elements not activated by the first or second waveforms because of destructive interaction with the first and second waveforms. According to some embodiments, the indicium of one or more interactions indicates a first center point of stimulation (CPS) arising from the first stimulation waveform and a second CPS arising from the second stimulation waveform. According to some embodiments, the processor is further configured to: receive input from a user specifying a change of one or more of the first and second stimulation waveforms as a function of time, and cause the GUI to display a time-resolved representation of a variance of the at least one indicium changes as a function of time. According to some embodiments, the time-resolved representation of the variance of the at least one indicium reflects a constructive or destructive interaction of the first and second waveforms within the patient's anatomy. According to some embodiments, the at least one indicium comprises: a first volume of activation (VOA) arising from the first waveform, a second VOA arising from the second waveform, and a third VOA arising from constructive activation by the first and second waveforms. According to some embodiments, the at least one indicium comprises a representation of one or more electric fields induced by the first and second waveforms. According to some embodiments, the at least one indicium indicates an activation function. According to some embodiments, causing the GUI to display at least one indicium of one or more interactions of the first and second stimulation waveforms with the patient's anatomy comprises: determining at least one electric field elicited in the patient's anatomy by the first and second stimulation waveforms, and determining one or more interactions of the electric field with at least one neural element of the patient's anatomy based on a neuronal model, wherein the neuronal model comprises a plurality of neuronal networks and models spatiotemporal interactions between the neuronal networks. According to some embodiments, the at least one indicium indicates neural activation of the at least one neural element. According to some embodiments, the processor is further configured to determine a therapeutic mechanism of action (MOA) correlated with the one or more interactions of the first and second stimulation waveforms with the patient's anatomy, and cause the GUI to display at least one indicium of the MOA. According to some embodiments, the displayed indicium of the MOA reflects a preferential activation of a first neural fiber type compared to other neural fiber types. According to some embodiments, the displayed indicium of the MOA reflects a presence or absence of paresthesia.

Also disclosed herein is a non-transitory computer-readable medium, comprising instructions executable by a processor of an external device for programming an implantable medical device (IMD) implantable in a patient, wherein the IMD comprises an implantable pulse generator (IPG) and one or more lead wires each comprising a plurality of electrodes. According to some embodiments the instructions, when executed by the processor, configure the processor to: render a graphical user interface (GUI) on a screen of the external device, cause the GUI to display a representation of the patient's anatomy, receive input from a user indicating at least a first stimulation waveform to be applied at a first one or more electrodes of the plurality of electrodes and a second stimulation waveform to be applied at a second one or more electrodes of the plurality of electrodes, and cause the GUI to display at least one indicium of one or more interactions of the first and second stimulation waveforms with the patient's anatomy. According to some embodiments, the indicium of one or more interactions indicates a constructive activation of neural elements within the patient's anatomy by the first and second waveforms. According to some embodiments, the indicium of one or more interactions indicates a region of the patient's anatomy comprising neural elements not activated by the first or second waveforms because of destructive interaction with the first and second waveforms. According to some embodiments, the indicium of one or more interactions indicates a first center point of stimulation (CPS) arising from the first stimulation waveform and a second CPS arising from the second stimulation waveform. According to some embodiments, the processor is further configured to: receive input from a user specifying a change of one or more of the first and second stimulation waveforms as a function of time, and cause the GUI to display a time-resolved representation of a variance of the at least one indicium changes as a function of time. According to some embodiments, the time-resolved representation of the variance of the at least one indicium reflects a constructive or destructive interaction of the first and second waveforms within the patient's anatomy. According to some embodiments, the at least one indicium comprises: a first volume of activation (VOA) arising from the first waveform, a second VOA arising from the second waveform, and a third VOA arising from constructive activation by the first and second waveforms. According to some embodiments, the at least one indicium comprises a representation of one or more electric fields induced by the first and second waveforms. According to some embodiments, the at least one indicium indicates an activation function. According to some embodiments, causing the GUI to display at least one indicium of one or more interactions of the first and second stimulation waveforms with the patient's anatomy comprises: determining at least one electric field elicited in the patient's anatomy by the first and second stimulation waveforms, and determining one or more interactions of the electric field with at least one neural element of the patient's anatomy based on a neuronal model, wherein the neuronal model comprises a plurality of neuronal networks and models spatiotemporal interactions between the neuronal networks. According to some embodiments, the at least one indicium indicates neural activation of the at least one neural element. According to some embodiments, the processor is further configured to determine a therapeutic mechanism of action (MOA) correlated with the one or more interactions of the first and second stimulation waveforms with the patient's anatomy, and cause the GUI to display at least one indicium of the MOA. According to some embodiments, the displayed indicium of the MOA reflects a preferential activation of a first neural fiber type compared to other neural fiber types. According to some embodiments, the displayed indicium of the MOA reflects a presence or absence of paresthesia.

Methods of programming an implantable medical device (IMD) are also disclosed. According to some embodiments, the IMD comprising an implantable pulse generator (IPG) and one or more lead wires each comprising a plurality of electrodes. Some embodiments of the method comprises: presenting a graphical user interface (GUI) on a display, causing the GUI to display a representation of the patient's anatomy, receiving input from a user indicating at least a first stimulation waveform to be applied at a first one or more electrodes of the plurality of electrodes and a second stimulation waveform to be applied at a second one or more electrodes of the plurality of electrodes, and causing the GUI to display at least one indicium of one or more interactions of the first and second stimulation waveforms with the patient's anatomy. According to some embodiments, the indicium of one or more interactions indicates a constructive activation of neural elements within the patient's anatomy by the first and second waveforms. According to some embodiments, the indicium of one or more interactions indicates a region of the patient's anatomy comprising neural elements not activated by the first or second waveforms because of destructive interaction with the first and second waveforms. According to some embodiments, the indicium of one or more interactions indicates a first center point of stimulation (CPS) arising from the first stimulation waveform and a second CPS arising from the second stimulation waveform. According to some embodiments, the method further comprises: receiving input from a user specifying a change of one or more of the first and second stimulation waveforms as a function of time, and causing the GUI to display a time-resolved representation of a variance of the at least one indicium changes as a function of time. According to some embodiments, the time-resolved representation of the variance of the at least one indicium reflects a constructive or destructive interaction of the first and second waveforms within the patient's anatomy. According to some embodiments, the at least one indicium comprises: a first volume of activation (VOA) arising from the first waveform, a second VOA arising from the second waveform, and a third VOA arising from constructive activation by the first and second waveforms. According to some embodiments, the at least one indicium comprises a representation of one or more electric fields induced by the first and second waveforms. According to some embodiments, the at least one indicium indicates an activation function. According to some embodiments, causing the GUI to display at least one indicium of one or more interactions of the first and second stimulation waveforms with the patient's anatomy comprises: determining at least one electric field elicited in the patient's anatomy by the first and second stimulation waveforms, and determining one or more interactions of the electric field with at least one neural element of the patient's anatomy based on a neuronal model, wherein the neuronal model comprises a plurality of neuronal networks and models spatiotemporal interactions between the neuronal networks. According to some embodiments, the at least one indicium indicates neural activation of the at least one neural element. According to some embodiments, the method further comprises determining a therapeutic mechanism of action (MOA) correlated with the one or more interactions of the first and second stimulation waveforms with the patient's anatomy, and causing the GUI to display at least one indicium of the MOA. According to some embodiments, the displayed indicium of the MOA reflects a preferential activation of a first neural fiber type compared to other neural fiber types. According to some embodiments, the displayed indicium of the MOA reflects a presence or absence of paresthesia.

BRIEF DESCRIPTION OF THE DRAWINGS

FIG. 1 shows an implantable pulse generator (IPG).

FIG. 2 shows a cross section of the IPG of FIG. 1 as implanted in a patient, as well as external devices that support the IPG, including an external charger and external controller.

DETAILED DESCRIPTION

Figure 3:
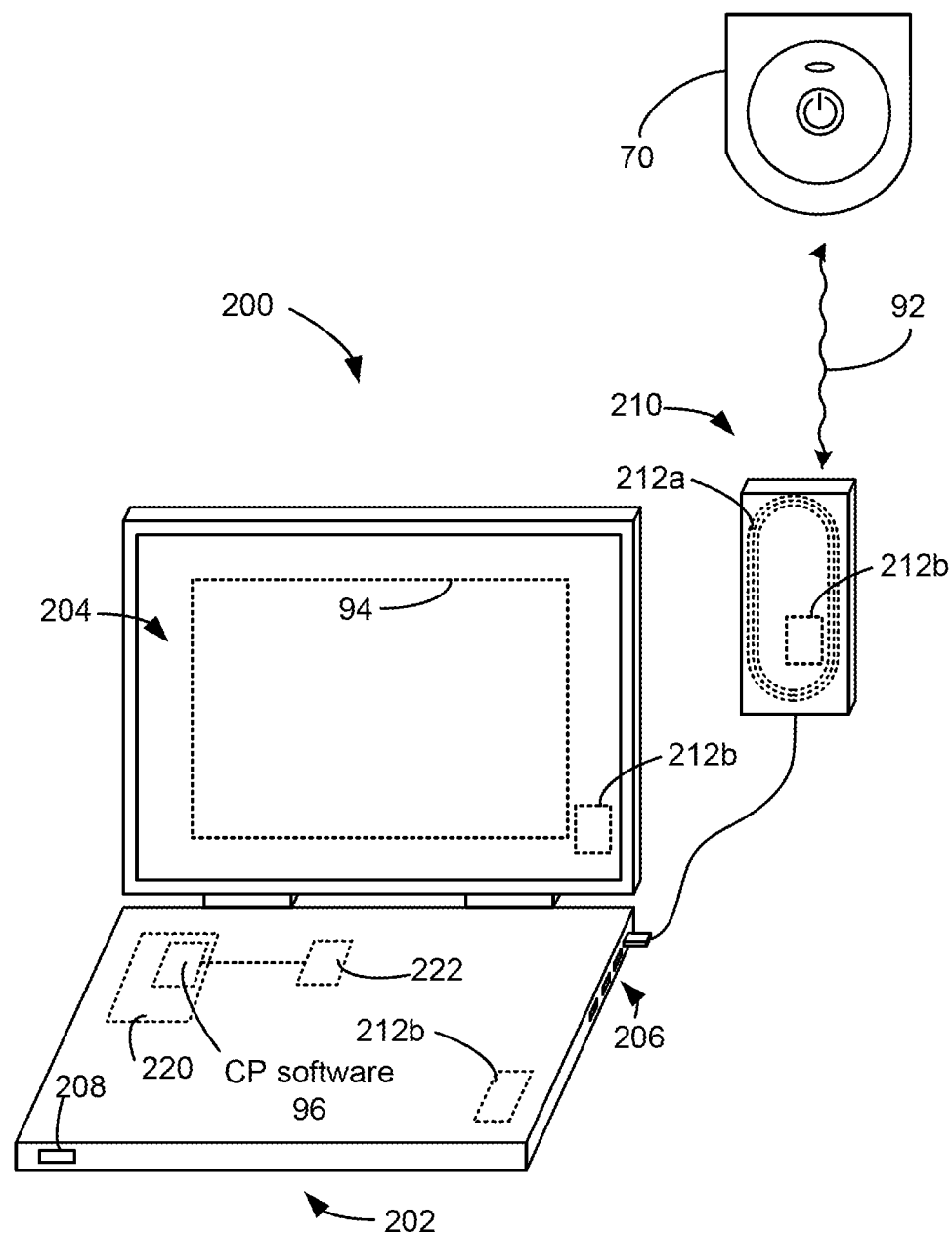
FIG. 3 shows components of a clinician's programmer system, including components for communicating with an external trial stimulator in accordance with an example of the disclosure.

As shown in FIG. 1, a traditional SCS system includes an implantable neurostimulator such as an Implantable Pulse Generator (IPG) 10, which includes a device case 12 that is formed from a biocompatible material such as titanium. The case 12 typically holds the circuitry and battery 14 (FIG. 2) necessary for the IPG 10 to function, which battery 14 may be either rechargeable or primary in nature. The IPG 10 delivers electrical stimulation to a patient's nerves and tissues through electrodes 16, which, in a SCS system are typically implantable within the epidural space within the spinal column. Common electrode arrangements include a linear arrangement along a percutaneous lead 18 and a two-dimensional arrangement on a paddle lead 60. The proximal ends of the leads 18 and 60 include lead connectors 20 that are connectable to the IPG 10 at one or more connector blocks 22 fixed in a header 24, which can comprise an epoxy, for example. Contacts in the connector blocks 22 make contact with electrode terminals in the lead connectors 20 and communicate with the circuitry inside the case 12 via feedthrough pins 26 passing through a hermetic feedthrough 28 to allow such circuitry to provide stimulation to or monitor the various electrodes 16. The number and arrangement of electrodes 16 on a percutaneous lead 18 or a paddle lead 60 can vary. When percutaneous leads 18 are employed, it is common for multiple such leads 18 to be implanted at different anatomical locations along the spinal canal.

As shown in FIG. 2, IPG 10 contains a charging coil 30 for wireless charging of the IPG's battery 14 using an external charger 50, assuming that battery 14 is a rechargeable battery. If IPG 10 has a non-rechargeable (primary) battery 14, charging coil 30 in the IPG 10 and the external charger 50 can be eliminated. IPG 10 also contains a telemetry coil antenna 32 for wirelessly communicating data with an external controller device 40, which is explained further below. In other examples, antenna 32 can comprise a short-range RF antenna such as a slot, patch, or wire antenna. IPG 10 also contains control circuitry such as a microcontroller 34, and one or more Application Specific Integrated Circuit (ASICs) 36, which can be as described for example in U.S. Pat. No. 8,768,453. ASIC(s) 36 can include stimulation circuitry for providing stimulation pulses at one or more of the electrodes 16 and may also include telemetry modulation and demodulation circuitry for enabling bidirectional wireless communications at antenna 32, battery charging and protection circuitry coupleable to charging coil 30, DC-blocking capacitors in each of the current paths proceeding to the electrodes 16, etc. Components within the case 12 are integrated via a printed circuit board (PCB) 38.

FIG. 2 further shows the external devices referenced above, which may be used to communicate with the IPG 10, in plan and cross section views. External controller (or, remote controller) 40 may be used to control and monitor the IPG 10 via a bidirectional wireless communication link 42 that passes through a patient's tissue 5. For example, the external controller 40 may be used to provide or adjust a stimulation program for the IPG 10 to execute that provides stimulation to the patient. The stimulation program includes a number of stimulation parameters, such as which electrodes are selected for stimulation; whether such active electrodes are to act as anodes or cathodes; and the amplitude (e.g., current), frequency, and duration of stimulation at the active electrodes, assuming such stimulation comprises stimulation pulses as is typical.

Communication on link 42 can occur via magnetic inductive coupling between a coil antenna 44 in the external controller 40 and the IPG 10's telemetry coil 32 as is well known. Typically, the magnetic field comprising link 42 is modulated, for example via Frequency Shift Keying (FSK) or the like, to encode transmitted data. For example, data telemetry via FSK can occur around a center frequency of fc=125 kHz, with a 129 kHz signal representing transmission of a logic '1' bit and a 121 kHz signal representing a logic '0' bit. However, transcutaneous communications on link 42 need not be by magnetic induction, and may comprise short-range RF telemetry (e.g., Bluetooth, WiFi, Zigbee, MICS, etc.) if antennas 44 and 32 and their associated communication circuitry are so configured. The external controller 40 is generally similar to a cell phone and includes a hand-holdable, portable housing.

External charger 50 provides power to recharge the IPG's battery 14 should that battery be rechargeable. Such power transfer occurs by energizing a charging coil 54 in the external charger 50, which produces a magnetic field comprising transcutaneous link 52, which may occur with a different frequency ($f_2$=80 kHz) than data communications on link 42. This magnetic field 52 energizes the charging coil 30 in the IPG 10, and the induced voltage is rectified, filtered, and used to recharge the battery 14. Link 52, like link 42, can be bidirectional to allow the IPG 10 to report status information back to the external charger 50, such as by using Load Shift Keying as is well-known. For example, once circuitry in the IPG 10 detects that the battery 14 is fully charged, it can cause charging coil 30 to signal that fact back to the external charger 50 so that charging can cease. Like the external controller 40, external charger 50 generally comprises a hand-holdable and portable housing.

External controller 40 and external charger 50 are described in further detail in U.S. Patent Application Publication 2015/0080982. Note also that the external controller 40 and external charger 50 can be partially or fully integrated into a single external system, such as disclosed in U.S. Pat. Nos. 8,335,569 and 8,498,716.

As mentioned above, the electrical stimulation that the IPG 10 is capable of delivering is highly customizable with respect to selected electrodes, electrode current amplitude and polarity, pulse duration, pulse frequency, etc. Due to uncertainties in the location of electrodes with respect to neural targets, the physiological response of a patient to stimulation patterns, and the nature of the electrical environment within which the electrodes are positioned, it is essentially impossible to determine the stimulation parameters that might provide effective stimulation therapy for a particular patient prior to implementing stimulation therapy. Thus, in order to determine whether the IPG 10 is capable of delivering effective therapy, and, if so, the stimulation parameters that define such effective therapy, the patient's response to different stimulation parameters is typically evaluated during a trial stimulation phase prior to the permanent implantation of the IPG 10.

During the trial stimulation phase, the distal ends of the lead(s) are implanted within the epidural space along the spinal cord while the proximal ends of the lead(s), including the electrode terminals 20, are ultimately coupled to an external neurostimulator such as external trial stimulator (ETS) 70, which is not implanted in the patient. The ETS 70, which is shown in FIG. 3, essentially mimics operation of the IPG 10 to provide stimulation to the implanted electrodes 16. This allows the effectiveness of stimulation therapy, such as whether therapy has alleviated the patient's symptoms, to be verified. Trial stimulation using the ETS 70 further allows for the determination of a particular stimulation program that seems promising for the patient to use once the IPG 10 is later implanted into the patient.

The stimulation program executed by the ETS 70 can be provided or adjusted via a wired or wireless link (wireless link 92 shown) from an additional external device known as a clinician's programmer 200, which includes features (described below) that enable a clinician to hone in on the appropriate stimulation therapy settings. As shown, CP system 200 can comprise a computing device 202, such as a desktop, laptop, or notebook computer, a tablet, a mobile smart phone, a Personal Data Assistant (PDA)-type mobile computing device, etc. (hereinafter "CP computer"). In FIG. 3, CP computer 202 is shown as a laptop computer that includes typical computer user interface means such as a screen 204, a mouse, a keyboard, speakers, a stylus, a printer, etc., not all of which are shown for convenience. Also shown in FIG. 3 is a communication head 210, which is coupleable to a suitable port on the CP computer 202, such as a USB port 206, for example. While the CP system is shown in communication with the ETS 70, the CP system 200 is also configured to communicate with the IPG 10 once it is implanted.

Communication between the CP system 200 and the ETS 70 or IPG 10 may comprise magnetic inductive or short-range RF telemetry schemes as already described, and in this regard the ETS 70 and the CP computer 202 and/or the communication head 210 (which can be placed proximate to the IPG 10 or ETS 70) may include antennas compliant with the telemetry means chosen. For example, the communication head 210 can include a coil antenna 212a, a short-range RF antenna 212b, or both. The CP computer 202 may also communicate directly with the IPG 10 of the ETS 70, for example using an integral short-range RF antenna 212b.

If the CP system 200 includes a short-range RF antenna (either in CP computer 202 or communication head 210), such antenna can also be used to establish communication between the CP system 200 and other devices, and ultimately to larger communication networks such as the Internet. The CP system 200 can typically also communicate with such other networks via a wired link provided at an Ethernet or network port 208 on the CP computer 202, or with other devices or networks using other wired connections (e.g., at USB ports 206).

To program stimulation parameters, the clinician interfaces with a clinician's programmer graphical user interface (CP GUI) 94 provided on the display 204 of the CP computer 202. As one skilled in the art understands, the CP GUI 94 can be rendered by execution of CP software 96 on the CP computer 202, which software may be stored in the CP computer's non-volatile memory 220. Such non-volatile memory 220 may include one or more non-transitory computer-readable storage mediums including, for example, magnetic disks (fixed, floppy, and removable) and tape, optical media such as CD-ROMs and digital video disks (DVDs), and semiconductor memory devices such as Electrically Programmable Read-Only Memory (EPROM), Electrically Erasable Programmable Read-Only Memory (EEPROM), and USB or thumb drive. One skilled in the art will additionally recognize that execution of the CP software 96 in the CP computer 202 can be facilitated by control circuitry 222 such as a microprocessor, microcomputer, an FPGA, other digital logic structures, etc., which is capable of executing programs in a computing device. Such control circuitry 222 when executing the CP software 96 will in addition to rendering the CP GUI 94 enable communications with the ETS 70 through a suitable antenna 212a or 212b, either in the communication head 210 or the CP computer 202 as explained earlier, so that the clinician can use the CP GUI 94 to communicate the stimulation parameters to the ETS 70.

Figure 4:
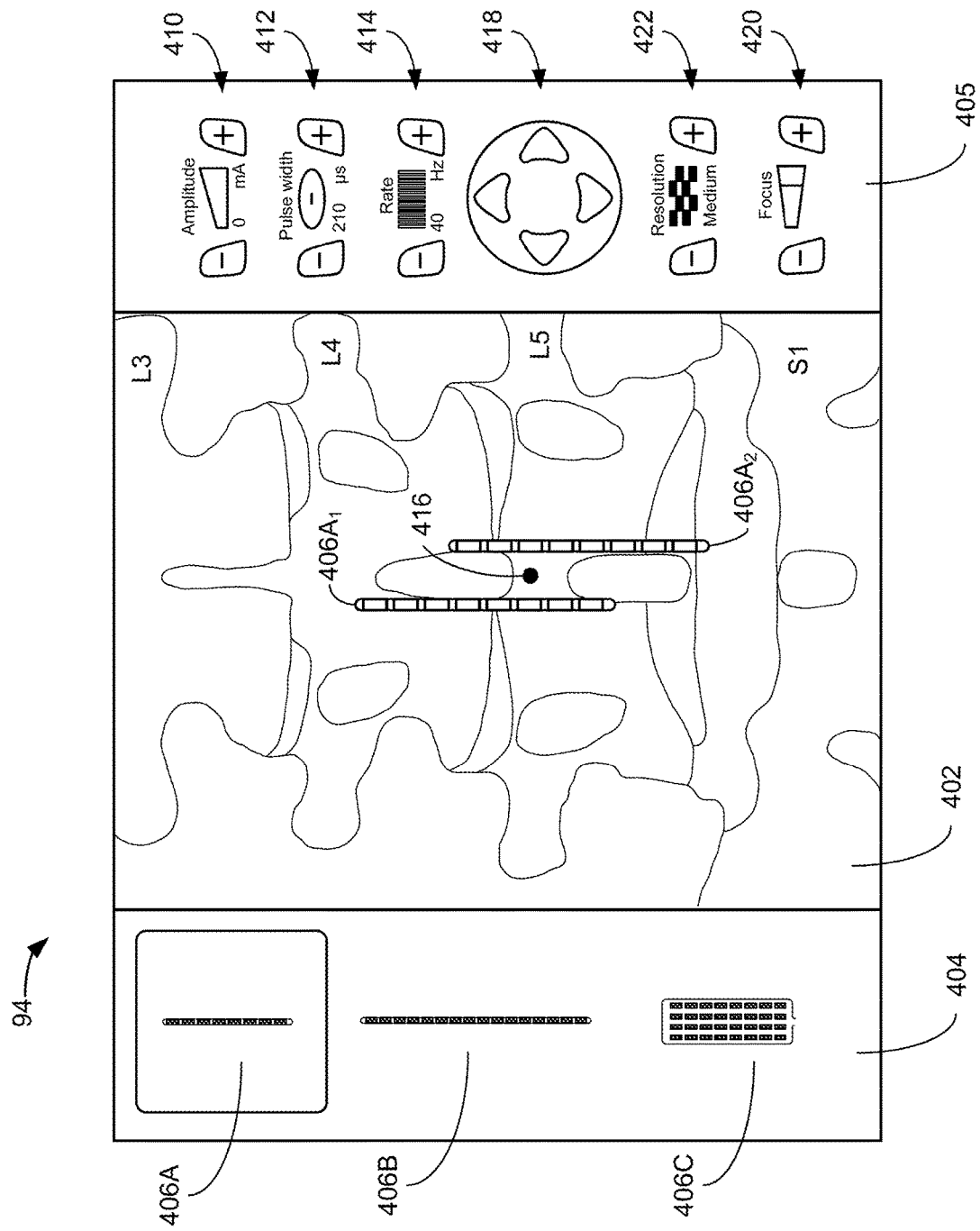
FIG. 4 shows an example of a graphical user interface that can be provided on the clinician's programmer system in accordance with an example of the disclosure.

An example of a portion of the CP GUI 94 is shown in FIG. 4. The illustrated portion of the GUI 94 includes fluoroscopic image 402, which shows the implanted leads relative to anatomical structures, such as vertebrae. Using the illustrated interface, a user can select a representation 406 of the implanted electrode lead from the lead interface 404, which includes representations 406 of various types of lead products such as 1×8 percutaneous lead representation 406A, 1×16 percutaneous lead representation 406B, and 4×8 paddle lead representation 406C. The user can then drag the selected lead representation 406 onto the fluoroscopic image 402 and manipulate its size and orientation until it aligns with the implanted electrode lead in the image 402. Because the representations 406 are programmed with properties of the lead such as electrode size, shape, and spacing, the positioning of a lead representation 406 over its corresponding implanted lead in the fluoroscopic image 402 relates the locations of the electrodes to the image 402. This enables a user to subsequently visualize through the GUI 94 the anatomical location of electrical stimulation as described below. Relative electrode locations can also be determined absent an image through measurements of inter-electrode impedance and voltages induced at electrodes by stimulation at other electrodes.

Such anatomical visualization of electrical stimulation can be beneficial in determining the desired stimulation program due to the spatial relationship between the point of stimulation and the location at which the effect of stimulation is perceived by a patient. While the precise mechanism by which spinal cord stimulation interrupts the sensation of pain is not fully understood, it is understood that the stimulation of a spinal nerve on a particular side of a patient's body results in the perception of stimulation (or simply the interruption of what was previously perceived as pain) on the same side of the body. For example, pain in the upper right leg, which is perceived as a result of the transmission of a neurological signal through sensory neurons from the location of the pain through a spinal nerve on the same side of the body and into the spinal cord where it is further transmitted to the brain, is interrupted by the application of electrical stimulation to the spinal nerve through which the pain signal travels (i.e., the spinal nerve on the right side of the body). Therefore, the visualization of the anatomical point of stimulation provides information that can guide the user in determining the appropriate stimulation parameters to treat a patient's particular pain symptoms.

Various inputs regarding the location and properties of stimulation can be provided by the user through interactive elements in the stimulation interface 405 of the GUI 94 as further illustrated in FIG. 4. The stimulation amplitude, pulse width, and frequency can be adjusted using the buttons 410, 412, and 414, respectively. The center point 416 of the desired stimulation field can be moved horizontally and vertically using the arrows 418. The shape of the target stimulation field can be customized, but, in one example, the target stimulation field may be represented by a tripole consisting of a target cathode at the center point of stimulation and two target anodes at equal distances from the cathode along a line that is parallel with the anatomical midline (i.e. along a vertical line in the interface 94). The focus of the target stimulation field, which is the distance between the target cathode and each target anode, can be adjusted using the focus buttons 420. The magnitude of the adjustments that are affected via the arrows 418 and the focus buttons 420 can be set at different granularity levels (e.g., coarse, medium, and fine) via the resolution buttons 422.

Aspects of the instant disclosure relate to the CP software 96, including the CP GUI 94. Specifically, aspects of the disclosed CP software 96 allow a clinician to use the CP GUI 94 to control and visualize spatiotemporal aspects of the stimulation waveforms and fields applied during therapy and to visualize spatiotemporal aspects neuronal excitation/modulation resulting from the applied stimulus. The CP software 96 includes realistic mathematical models that include spatiotemporal interactions of the patient's neuronal networks. This allow realistic time-resolved visualization of such interactions in real time and/or pseudo real time and can guide the clinician in the selection of individually tailored therapeutic paradigms.

Figure 5:
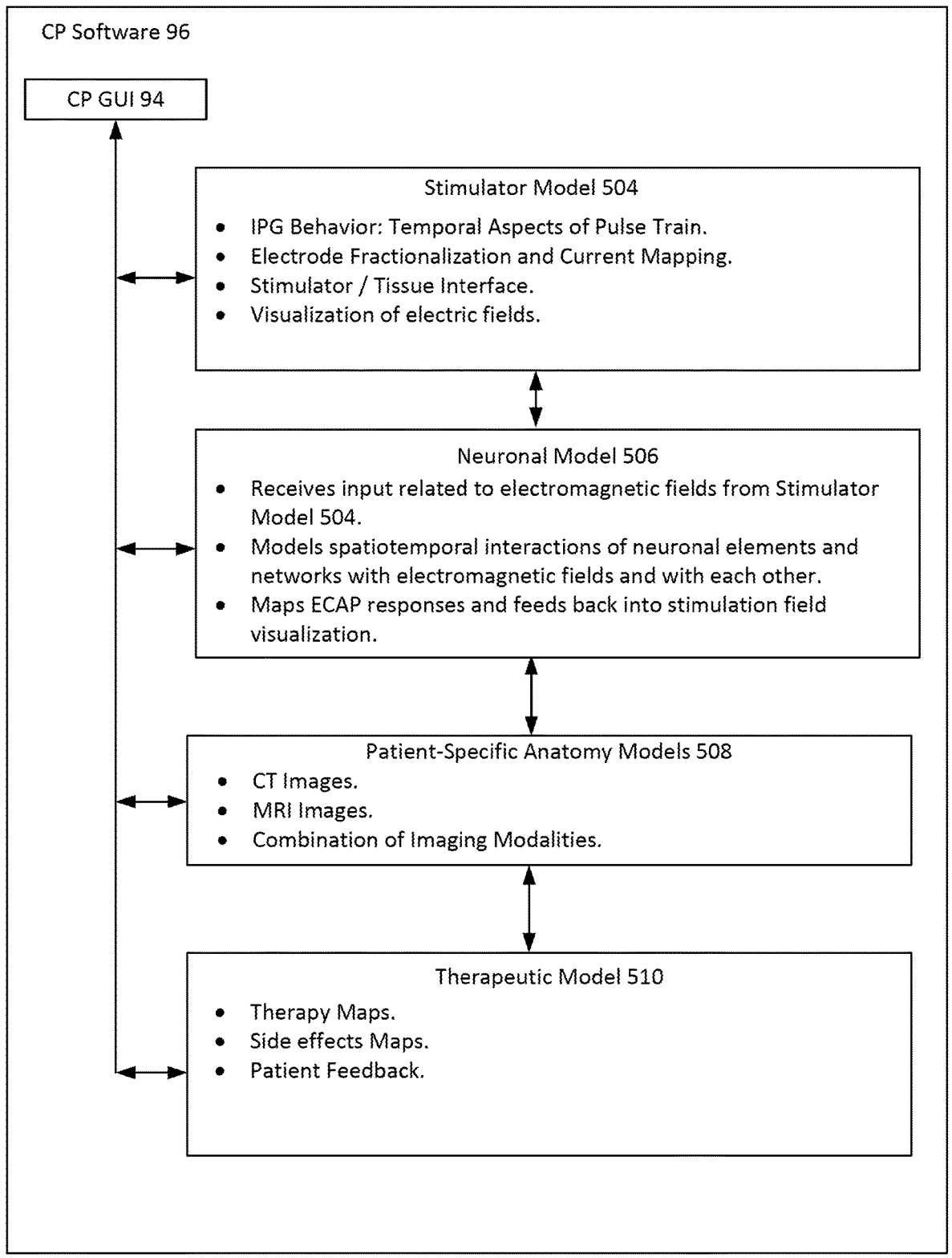
FIG. 5 shows a logical schematic of a clinician's programmer software.

FIG. 5 illustrates a logical overview of an embodiment of the CP software 96. The CP software 96 includes a CP GUI 94. Some aspects of the CP GUI 94 have been discussed above and further aspects will become apparent based on the discussion below. The CP GUI 94 interacts with multiple models/modules contained within the CP software 96. The illustrated models/modules are a stimulator model 504, a neuronal model 506, patient-specific models 508, and therapeutic models 510. Each of these models/modules will be discussed here briefly and further aspects of their operation and interactions with each other will become apparent based on further discussion below. But before discussing the models/modules 504-510, it should be noted that while these models/modules are illustrated as separate logical entities, that may not necessarily be the case in all embodiments of the CP software 96. In other words, some aspects and/or functionality attributed to one model/module may be shared or distributed among multiple modules.

The stimulator model 504 models the stimulator behavior for a given set of stimulation parameters and models the stimulator/tissue interface. This allows a clinician using the CP GUI 94 to visualize and control the electric fields applied to the patient's neural tissues. The clinician can also use the CP GUI 94 to interact with the stimulator model 504. For example, the clinician can press buttons that effect the stimulation field(s) and the CP GUI 94 allows visualization/rendering after each button press or a sequence of fields shown with representative time intervals. According to some embodiments, the stimulator model 504 predicts and controls the behavior of the IPG, including temporal aspects of the electrical pulses provided by the IPG, such as temporal variations of amplitude, pulse width, and pulse width of the applied electrical stimulation. The stimulator model 504 can predict and calculate aspects of the stimulation fields elicited by the pulses, such as the center point of stimulation (CPS), the instantaneous energy and total energy imparted into a patient's tissue, residual charge residing in the neural tissue, and volume of activation (VOA). The stimulator model 504 interfaces with the CP GUI 94, allowing indications of these values to be displayed and visualized on the CP GUI 94. For example, the CPS might be displayed as a circle on the CP GUI 94. The VOA might be displayed as a shaded area, an iso-line, an iso-surface, or a heat map.

While the target stimulation field could be generated by providing stimulation at the locations of the target poles (i.e., the target cathode and target anodes), the target poles do not necessarily correspond to the location of physical electrodes. Thus, a current mapping algorithm, which is part of the stimulator model 504, is employed to compute the fraction of the total stimulation current that should be sourced to or sunk from each physical electrode to best represent the electric field that would result from stimulation at the target poles. The inputs to the current mapping algorithm are the positions and relative strengths of the target poles and the positions of the physical electrodes. From these inputs, the current mapping algorithm outputs the current fraction and polarity of current that should be delivered to each physical electrode (i.e., the electrode allocation) to mimic the target stimulation field as well as an amplitude change that is necessary to maintain stimulation intensity as is now briefly explained. These properties form part of the electrode configuration that can be communicated to the neurostimulator.

The stimulator model 504 includes a model (such as a finite element model) that can be used to evaluate properties of the electric field that would be generated as a result of stimulation at the target poles. As used herein, modeling an electric field or generating a model of an electric field refers to determining one or more electrical properties at different spatial locations. Similarly, an electric field model refers to the values of the one or more electrical properties at the different spatial locations. The electrical properties may include the magnitude and/or direction of the electric field itself, the magnitude of an electric potential, the magnitude of a current, or other electrical properties at the different spatial locations. Thus, an electric field model does not necessarily refer to values of the strength and direction of an electric field (as the model may include a collection of other electrical values such as electric potentials) and does not imply that values exist at every spatial location within a volume of tissue but rather at a determined number of locations.

Figures 6, 7A, 7B, 7C:
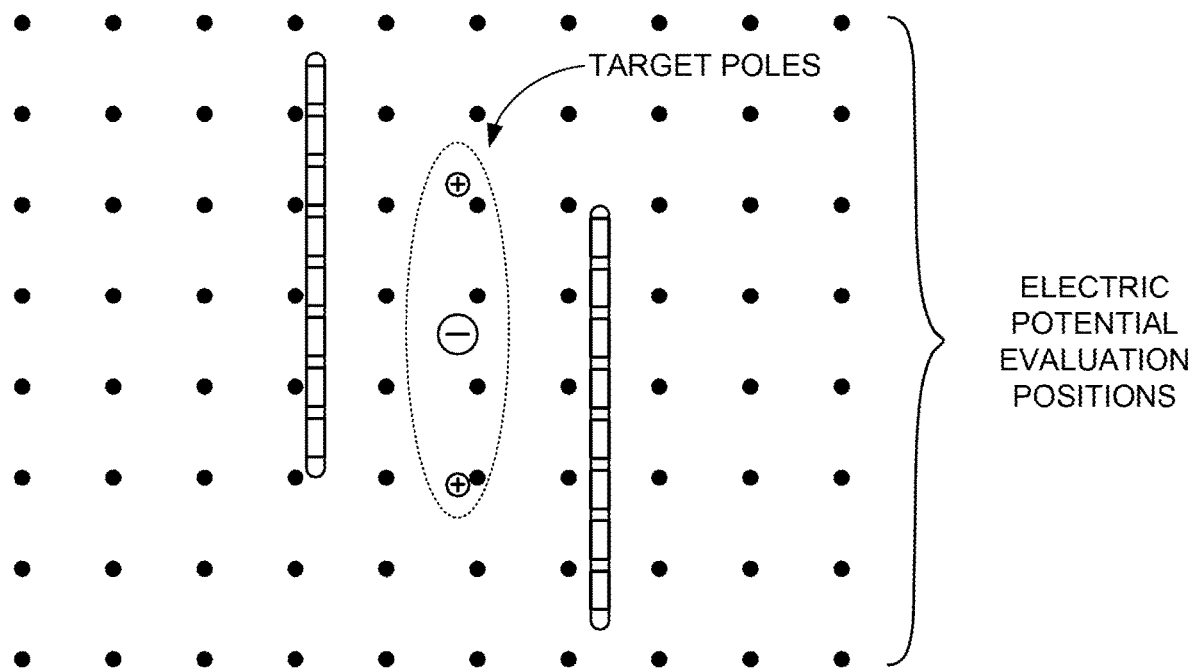
FIG. 6 illustrates a portion of the current mapping algorithm that is used to determine the fraction and polarity of electrodes that best matches a target stimulation field in accordance with an example of the disclosure.
FIGS. 7A-7C show the properties of different matrices that are used in the current mapping algorithm in accordance with an example of the disclosure.

In an example, the stimulator model 504 considers the electrical properties of different anatomical structures such as white matter, gray matter, cerebral spinal fluid, epidural space, dura, and vertebral bone in the area of the target poles to determine the electric potential that would be induced at each of m electric potential evaluation positions as a result of stimulation at the target poles. The electric potential evaluation positions may be arranged in a grid as shown in FIG. 6. While a small number of evaluation positions are shown for purposes of illustration, in an actual implementation the spatial resolution of the evaluation positions may be much higher. The modeled electric potentials at the m evaluation positions that would result from stimulation at the target poles form a m×1 vector, $\varphi$ (FIG. 7A).

The stimulator model 504 is also used to determine the electric potentials that would be induced at the in evaluation positions as a result of stimulation via n physical electrode arrangements. While the modeled electrode arrangements can include any combination of electrodes (e.g. bipoles, tripoles, etc.), in one example, the n electrode arrangements are each bipole arrangements (e.g., E1 is 100% cathode and E2 is 100% anode, E2 is 100% cathode and E3 is 100% anode, etc.). The electric potentials at the m evaluation positions that are determined as a result of modeling stimulation via the n electrode arrangements form a m×n transfer matrix, A (FIG. 7B). Any number of electrode arrangements can be modeled to increase the size of the transfer matrix A, and the solution accuracy and computational difficulty are both increased as the number of electrode arrangements n is increased.

The electric potentials that would be formed at the m evaluation positions as a result of a combination of various electrode arrangements can be determined by multiplying the transfer matrix A with a n×1 vector j (FIG. 7C) that specifies the proportions (X) of each of the n electrode arrangements. The combination of electrode arrangements that would induce electric potentials at the m evaluation positions that best match those generated as a result of stimulation at the target poles can be determined by solving for the value of j that minimizes the equation $|\varphi - Aj|^2$. The relative proportions of the electrode arrangements in the calculated value of j can be converted to the electrode current fractions and polarities that would result in an electric potential field that most closely mimics the target stimulation field.

Figure 8A:
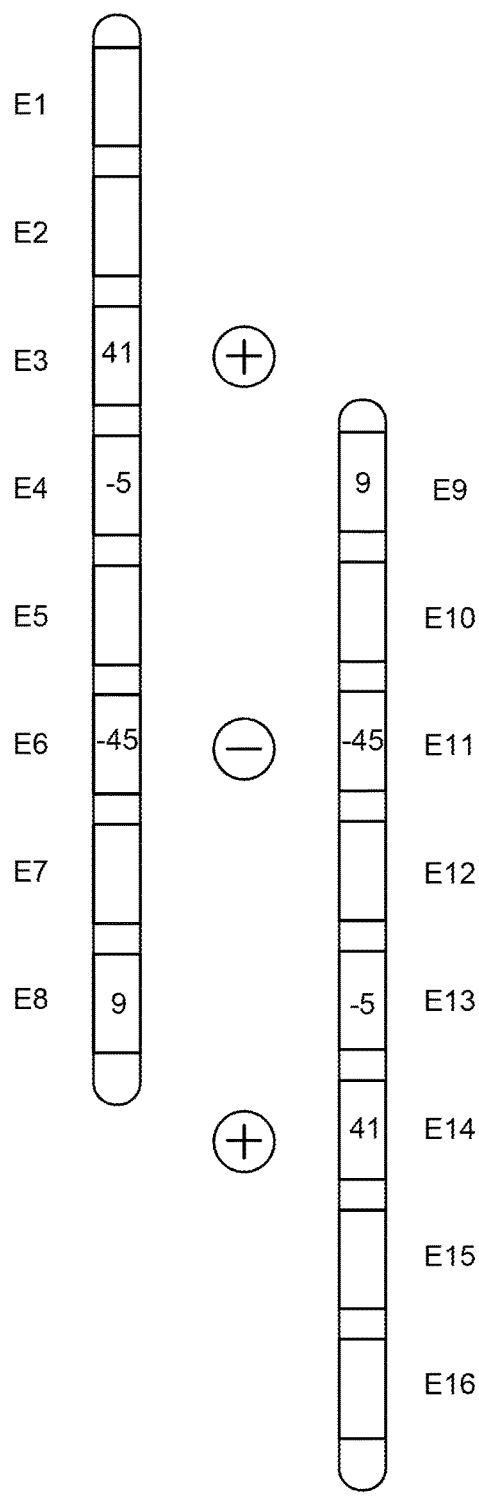
FIGS. 8A and 8B show examples of the determined allocation of current among electrodes for different target stimulation fields in accordance with an example of the disclosure.
Figure 8B:
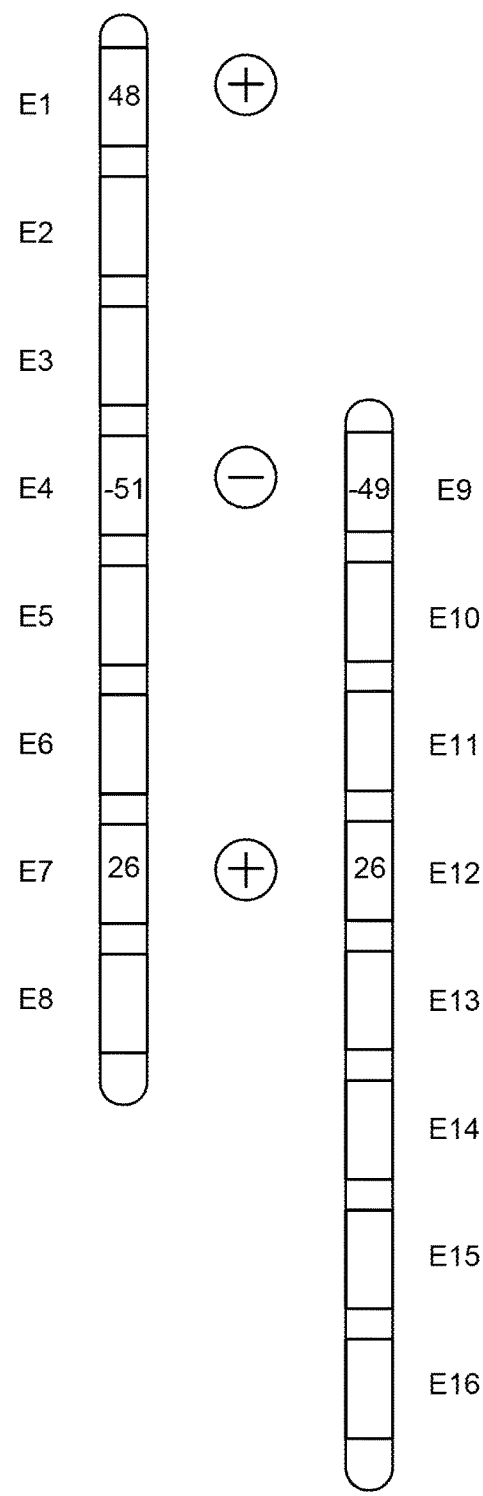

The current fractions and polarities that may be computed by the current mapping algorithm for example target stimulation fields are illustrated in FIGS. 8A and 8B. In the figures, two percutaneous leads are shown. The leads are offset by three electrodes with the left lead inserted further than the right lead. In FIG. 8A, the target stimulation field is represented by a tripole having a center point of stimulation that is positioned between electrodes E6 and E11 and a focus of three times the electrode-to-electrode spacing on the leads. The output of the current mapping algorithm specifies that the target stimulation field is best represented when 41% of the anodic current is allocated to each of electrodes E3 and E14, 9% of the anodic current is allocated to each of electrodes E8 and E9, 45% of the cathodic current is allocated to each of electrodes E6 and E11, and 5% of the cathodic current is allocated to each of electrodes E4 and E13. In FIG. 8B, the target stimulation field is represented by the same tripole as in FIG. 8A except the center point of stimulation is shifted such that it is positioned between electrodes E4 and E9. The output of the current mapping algorithm specifies that this target stimulation field is best represented when 51% of the anodic current is allocated to electrode E4, 49% of the anodic current is allocated to electrode E9, 26% of the cathodic current is allocated to each of electrodes E7 and E12, and 48% of the cathodic current is allocated to electrode E1. The determination of current fractions and polarities that best match a target stimulation field is described in greater detail in U.S. Pat. No. 8,412,345, which is incorporated herein by reference in its entirety.

In addition to determining the fraction and polarity of current that should be delivered to each electrode to best represent the target stimulation field, the current mapping algorithm additionally determines whether and to what extent the total stimulation amplitude should be adjusted to maintain constant stimulation intensity. The determined allocation of current between the electrodes is input to the model described above to determine the resulting spatial distribution of electric potentials for a baseline stimulation amplitude (e.g., total stimulation amplitude of 1 mA). The modeled potentials are assumed to scale linearly with increasing stimulation amplitude and are adjusted from the baseline amplitude to the actual stimulation amplitude that is being used.

Referring again to FIG. 5, the CP Software 96 also employs a neuronal model 506 that evaluates the response of neural elements to the electric fields induced by the applied stimulation. The neuronal model 506 incorporates morphological and electrical properties to evaluate the response of neural elements to the different electric field properties that are observed at different neural element evaluation positions. The neuronal model 506 includes mathematical models that include spatiotemporal interactions of neural subpopulations within the modeled neural network. In other words, the neuronal model 506 accounts for how activation, modulation, inhibition, or the like of one area within the modeled neural network may interact with responses of and from other areas.

The neuronal model 506 can receive input related to electromagnetic fields, e.g., voltage, current, magnetic flux, etc., at various locations within the modeled neural anatomy. Such input may be provided by the stimulator model 504. The neuronal model 506 may include modeled neural elements such as axons, dendrites, general fibers, cell bodies, glial cells, etc. The neuronal model 506 can include, for example, a non-linear neural element model, for example, that includes numerical integration. It can entail, for example, two or more interacting differential equations. It can be deterministic or probabilistic. Input to the neuronal model 506 can include voltage or another parameter derived from voltage, e.g., electric field (EF) or activating function (AF), at several positions of a neural element. An example of a neuronal model 506 is one that implements the software NEURON®. See Carnevale, N. T. et al., "The NEURON Book," Cambridge, UK: Cambridge University Press (2006).

The neuronal model 506 interacts with the CP GUI 94, allowing visualization of spatiotemporal interactions of the modeled neuronal populations/sub-populations with each other and with the electromagnetic fields generated based on the stimulator model 504. For example, the neuronal model 506 can indicate which of the neuronal populations are excited or inhibited by the electric fields. The neuronal model 506 can allow the CP GUI 94 to indicate particular fiber types or fiber sizes that are impacted by a set of stimulation parameters. For example, using one or more activation maps, different fiber types or sizes may be color coded in the CP GUI 94 and/or heat maps may indicate areas or neural subpopulations that are excited or inhibited. According to some embodiments, dorsal horn (DH) and dorsal column (DC) activation can be visualized using different colors in the CP GUI 94, allowing the clinician to adjust the stimulation parameters to preferentially activate one or the other. For example, by visualizing the stimulation fields and the resultant activations, the clinician can devise a stimulation that is constructive for targeting the DC but not the DH, or vise-versa.

Such interactions may also be time resolved, showing sequences of activations and/or how excitation/inhibition evolves with time, for example using time-lapse images. The neuronal model 506 can determine a VOA within the neural tissue and display the VOA on the CP GUI 94. As the neuronal model 506 includes modeling of how different neuronal subpopulations interact with each other, the determined VOA can consider co-relations between associated neural elements to determine how activation of different subpopulations reinforces each other or destructively interferes with each other, resulting in the calculated VOA, for example. The neuronal model 506 can also determine evoked compound action potentials (ECAPs) arising due to activation of neuronal subpopulations. The ECAPs can be mapped and visualized using the CP GUI 94. Moreover, the electric fields arising due to ECAPs can be fed back into the field calculations determined by the stimulator model 504 to further refine the electric fields visualized using the CP GUI 94.

The CP software 96 may also include one or more patient-specific anatomy models 508. The patient-specific anatomy models 508 may include or be informed by patient anatomy data derived by imaging modalities such as CT images, MRI images, or combinations of such imaging modalities. Patient-specific data provided by the patient-specific anatomy models 508 can be used to improve VOA computation provided by the neuronal model 506, for example.

The CP software 96 may include one or more therapeutic models 510, which are used to estimate the results of the chosen stimulation. The therapeutic models 510 determine relationships between the neural activation determined based on the stimulator model 504, neuronal model 506, and/or patient-specific anatomy models 508 and therapeutic outcomes resulting from the stimulation. The therapeutic models 510 may include one or more therapy maps and/or side effects maps, whereby activation of neuronal populations or subpopulations are correlated to a therapeutic results and/or side effects. Such therapeutic results might include pain alleviation or pain cessation for example. Side effects may include paresthesia, pain, or the like. The therapy maps/side effects maps may be included in look-up tables, for example. The therapeutic model 510 may be based on, or optimized based on, patient feedback.

By incorporating the modules/models described above, the CP software 96, as logically illustrated in FIG. 5, provides a clinician powerful tools for visualizing modalities of treatment using neuromodulation and for visualizing potential mechanisms of action (MOAs). The CP software allows a clinician to visualize electrical fields generated in the patient's tissues during stimulation, visualize interactions between the electrical fields, visualize the interactions of the electrical fields with the neural populations and subpopulations, visualize interactions between neural subpopulations, and visualize and predict how all these interactions may relate to therapeutic outcomes. Thus, the clinician can better predict efficacy and optimize patient outcome.

Figure 9:
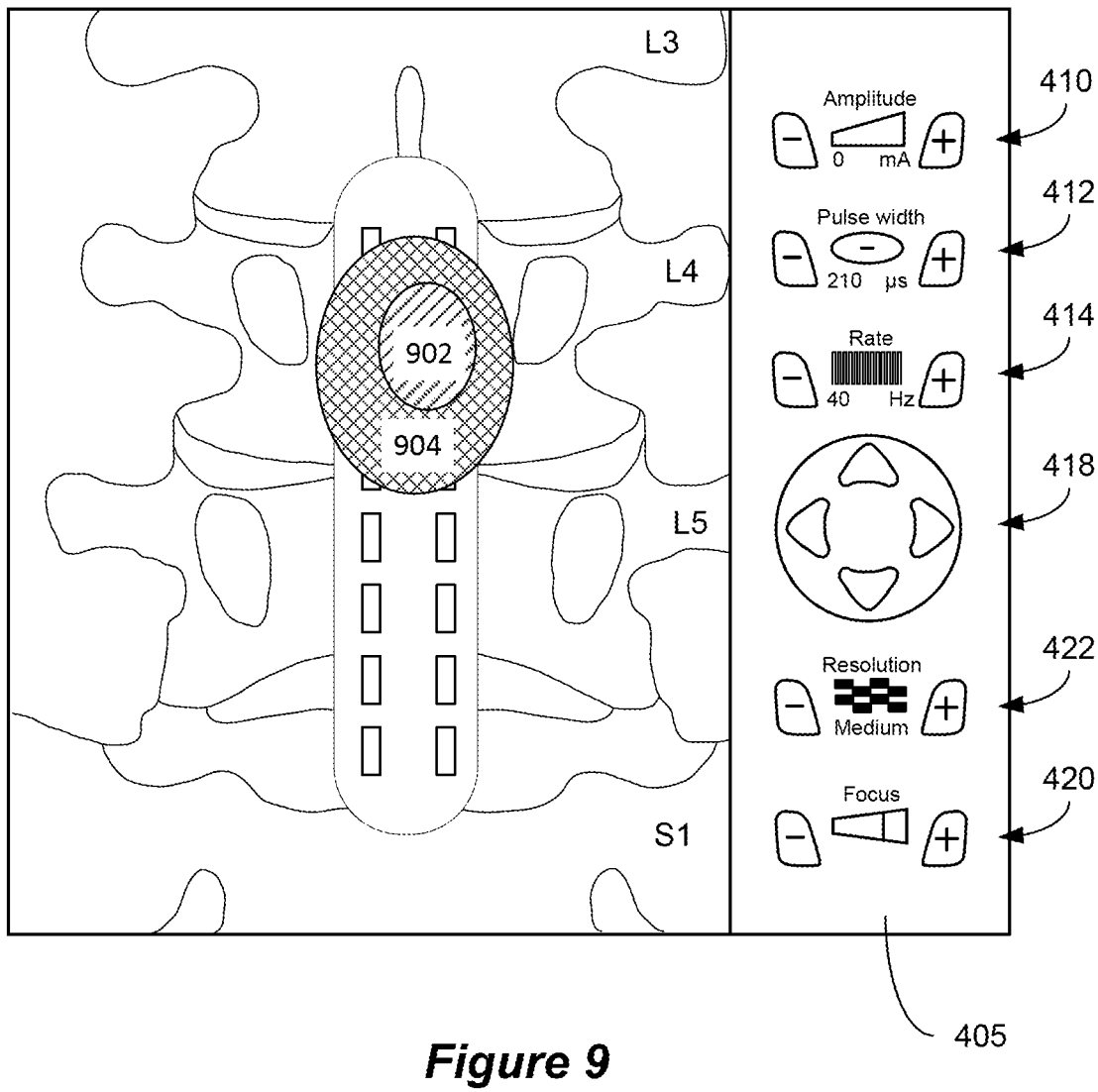
FIG. 9 shows an example of using aspects of a graphical user interface to visualize a volume of activation elicited by different stimulation waveforms.
Figure 10:
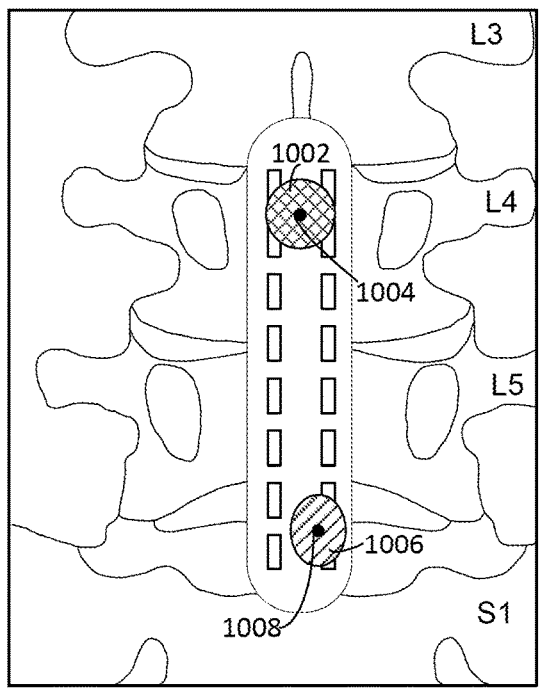
FIGS. 10A-10D show an example of using aspects of a graphical user interface to visualize the interaction of two stimulation waveforms.
Figure 10:
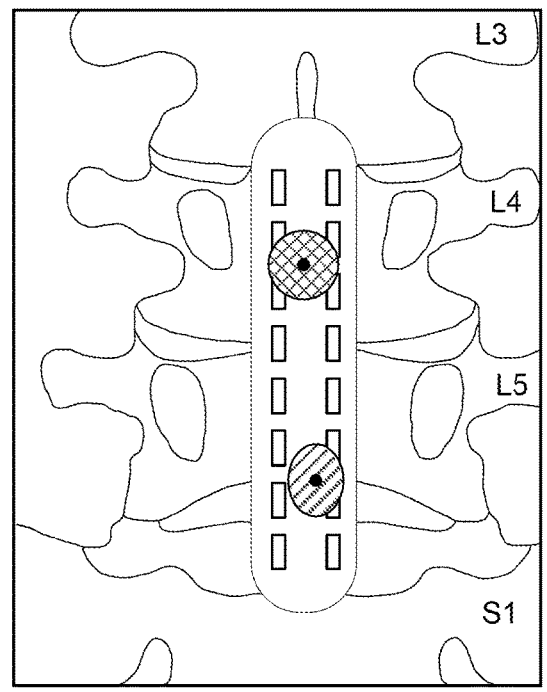
Figure 10:
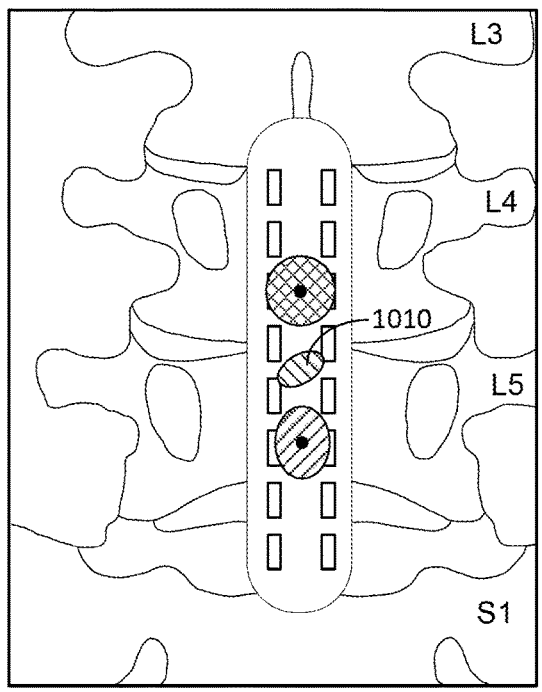
Figure 10:
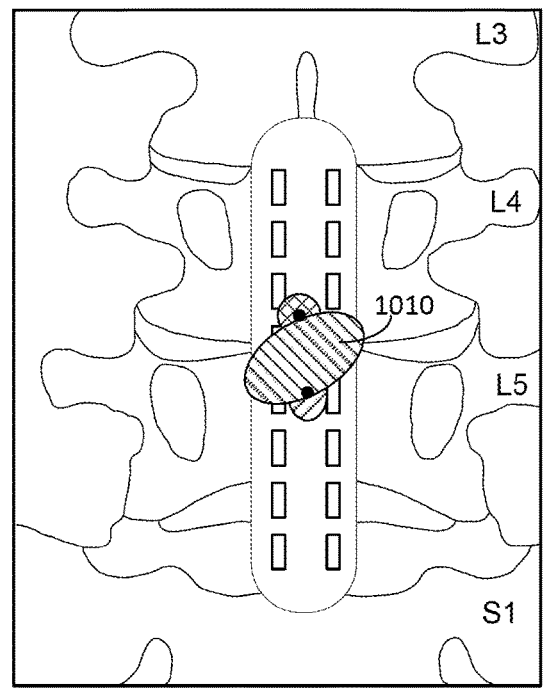

FIG. 9 illustrates an example of visualizing a volume of activation (VOA) corresponding to electrical stimulation applied at electrodes of a paddle lead using pulses having different pulse widths. Stimulation waveforms of different pulse widths may activate fibers having different diameters. Using the CP GUI 94, a clinician can adjust the pulse width of a stimulation waveform, for example, using buttons 412. For each given pulse width, the neuronal model 506 predicts which fibers are targeted and calculates a resulting VOA, which can be displayed in the CP GUI 94. In FIG. 9, the shaded area 902 might represent a VOA corresponding to a pulse width of 50 µs and the shaded area 904 might represent a VOA corresponding to a pulse width of 500 µs, for example.

FIGS. 10A-D illustrate an example of visualizing neural responses to two waveforms applied at different locations and how the activation of the neural populations change as the two locations are moved with respect to each other. Assume that shaded area 1002 is the VOA resulting from a first stimulation waveform applied at a CPS 1004 and that shaded area 1006 is the VOA resulting from a second stimulation waveform applied at a CPS 1008. Separately these waveforms elicit weak responses. But as the CPSs are brought closer together, the two waveforms elicit an additive response 1010, the magnitude of which increases become closer.

Figure 11:
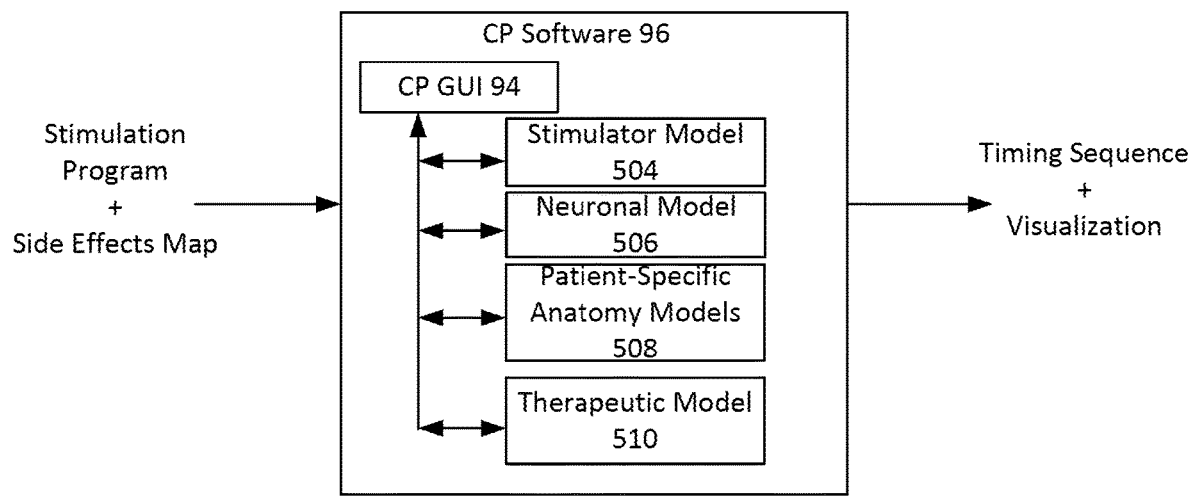
FIGS. 11A and 11B show an example of using a clinician's programmer software to visualize constructive and destructive stimulation.
Figure 11:
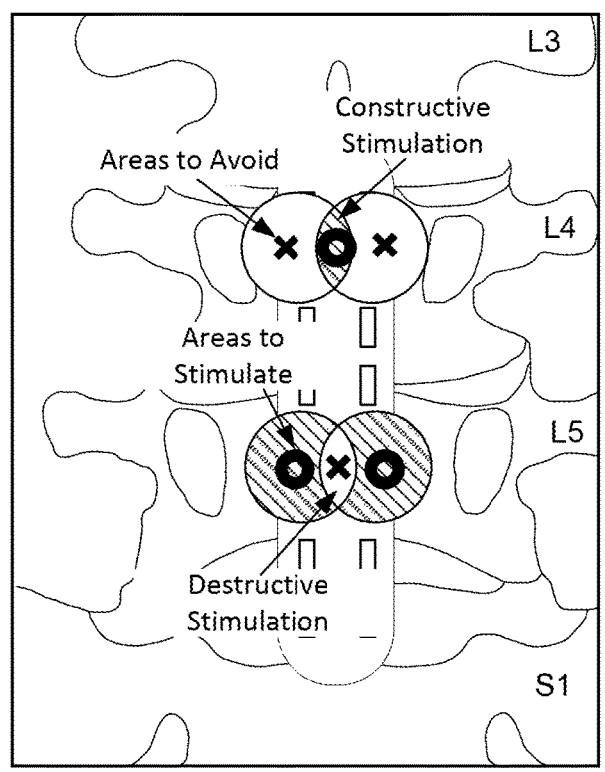

FIGS. 11A and 11B illustrates an embodiment of using the CP software 96 to visualize constructive and destructive activation application of electrical fields to preferentially stimulate areas of the patient's neural tissues that are associated with a therapeutically beneficial effect (areas indicated by the open circles) while avoiding stimulating areas that are associated with a side effect (areas indicated by the X). The areas to stimulate and areas to avoid are mapped and indicated on the CP GUI 94 based on the therapy maps and side effects maps contained within the therapeutic model 510. The clinician can use the CP GUI 94 to adjust the stimulation at the various electrodes to arrive at, and visualize, appropriate electrical stimulation waveforms that selectively target the appropriate neural populations. The stimulator model 504 interacting with neuronal model 506 calculates the timing of the stimulation pulse sequences that result in the desired stimulation fields and allows those fields to be displayed on the CP GUI 94. The clinician can modify and sculpt the fields using the CP GUI 94.

Figure 12:
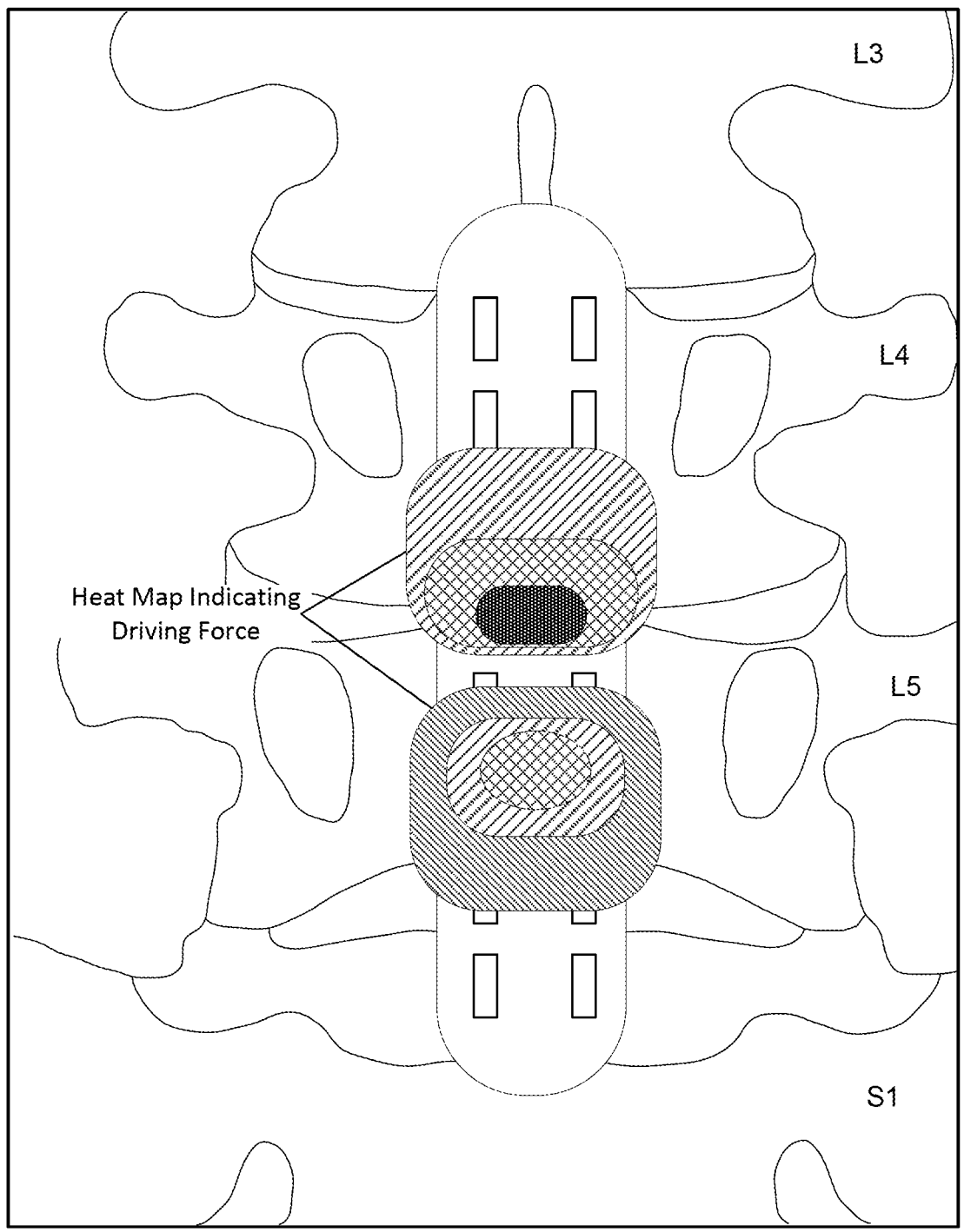
FIG. 12 shows an example of using aspects of a graphical user interface to visualize a neuronal driving force for neural stimulation.

FIG. 12 illustrates an embodiment of using the CP software 96 to visualize neuronal driving forces for preferentially targeting neural elements for stimulation. Using the CP GUI 94, a clinician can select or adjust parameter sets for conveying electrical modulation energy to the patient's tissue. The CP software can determine, based on patient anatomy, the stimulator model, and the neuronal model, the locus of one or more neuronal driving forces, with respect to the patient's neural anatomy. Indicators of the neuronal driving forces may be displayed on the CP GUI 94, for example, using a color-coded heat map. The neuronal driving forces may be one or more components of an electrical field or electrical field gradient generated by the stimulation. For example, in the case of spinal cord stimulation, as illustrated in FIG. 12, the electrical field component may be longitudinal or transverse to the spinal cord of the patient. Alternatively, transverse and longitudinal components of the electrical field may be represented as different colors in the CP GUI 94. Still alternatively, the neuronal driving force may be an activating function, for example, which may be determined by calculating the second-order spatial derivative of the extracellular potential along the axons, based on the neuronal model. According to some embodiments, the display of the CP GUI 94 can be toggled between modes displaying different neuronal driving forces. Visualization of neuronal driving forces, as illustrated in FIG. 12, can help a clinician determine parameter set, for example having fractionalized electrode combinations, for targeting specific neural targets, such as the dorsal horn (DH), dorsal column (DC), dorsal roots, and the like.

Figure 13:
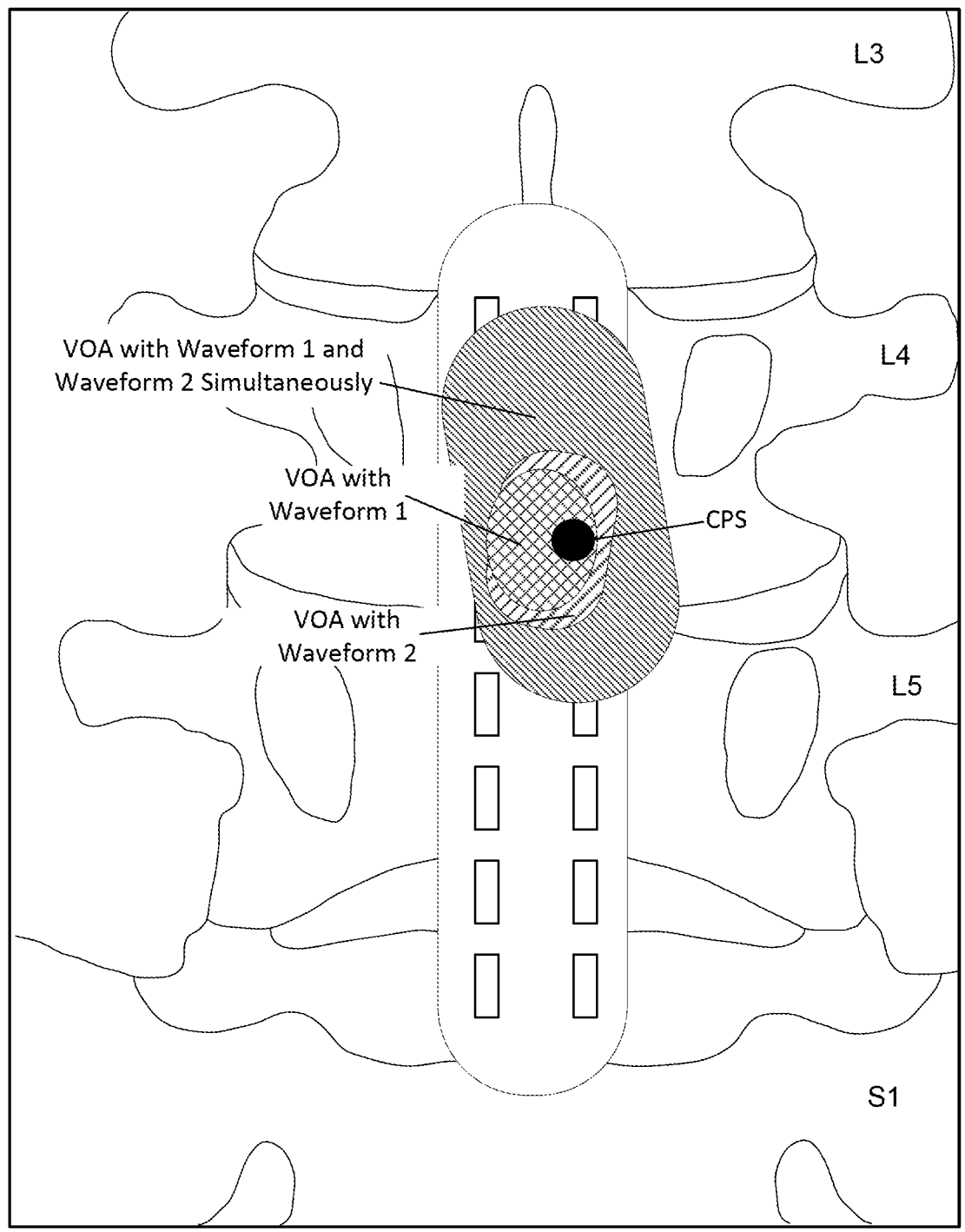
FIG. 13 shows an example of using aspects of a graphical user interface to visualize a volume of activation resulting from application of two stimulation waveforms.

FIG. 13 illustrates using the CP software 96 to visualize combination therapy, whereby two or more stimulation waveforms are applied at a center point of stimulation (CPS) (indicated by a black dot). The CP GUI 94 can display a first volume of activation (VOA) arising from the first stimulation waveform alone, a second VOA arising from the second stimulation waveform alone, and a third VOA arising from the combination of the first and stimulation waveforms. It should be noted that the two or more stimulation waveforms can be applied at the CPS simultaneously or they may be applied according to a timing sequence. The displayed VOA indicators can reflect how the VOA changes over time, depending on the timing sequence, for example.

While the invention herein disclosed has been described by means of specific embodiments and applications thereof, numerous modifications and variations could be made thereto by those skilled in the art without departing from the scope of the invention set forth in the claims.

What is claimed is:

1. An external device for programming an implantable medical device (IMD) implantable in a patient, the IMD comprising an implantable pulse generator (IPG) and one or more lead wires each comprising a plurality of electrodes, the external device comprising:
   a graphical user interface (GUI); and
   one or more processors configured to:
      cause the GUI to display a representation of the patient's anatomy,
      receive input from a user indicating at least a first stimulation waveform to be applied at a first one or more electrodes of the plurality of electrodes and a second stimulation waveform to be applied at a second one or more electrodes of the plurality of electrodes, and
      cause the GUI to display at least one indicium of one or more interactions of the combined first and second stimulation waveforms with the patient's anatomy.

2. The external device of claim 1, wherein the indicium of one or more interactions indicates a constructive activation of neural elements within the patient's anatomy by the first and second waveforms.

3. The external device of claim 1, wherein the indicium of one or more interactions indicates a region of the patient's anatomy comprising neural elements not activated by the first or second waveforms because of destructive interaction with the first and second waveforms.

4. The external device of claim 1, wherein the indicium of one or more interactions indicates a first center point of stimulation (CPS) arising from the first stimulation waveform and a second CPS arising from the second stimulation waveform.

5. The external device of claim 1, wherein the processor is further configured to:
receive input from a user specifying a change of one or more of the first and second stimulation waveforms as a function of time, and
cause the GUI to display a time-resolved representation of a variance of the at least one indicium changes as a function of time.

6. The external device of claim 5, wherein the time-resolved representation of the variance of the at least one indicium reflects a constructive or destructive interaction of the first and second waveforms within the patient's anatomy.

7. The external device of claim 1, wherein the at least one indicium comprises:
a first volume of activation (VOA) arising from the first waveform,
a second VOA arising from the second waveform, and
a third VOA arising from constructive activation by the first and second waveforms.

8. The external device of claim 1, wherein the at least one indicium comprises a representation of one or more electric fields induced by the first and second waveforms.

9. The external device of claim 1, wherein the at least one indicium indicates an activation function.

10. The external device of claim 1, wherein causing the GUI to display at least one indicium of one or more interactions of the first and second stimulation waveforms with the patient's anatomy comprises:
determining at least one electric field elicited in the patient's anatomy by the first and second stimulation waveforms, and
determining one or more interactions of the electric field with at least one neural element of the patient's anatomy based on a neuronal model, wherein the neuronal model comprises a plurality of neuronal networks and models spatiotemporal interactions between the neuronal networks.

11. The external device of claim 10, wherein the at least one indicium indicates neural activation of the at least one neural element.

12. The external device of claim 1, wherein the processor is further configured to determine a therapeutic mechanism of action (MOA) correlated with the one or more interactions of the first and second stimulation waveforms with the patient's anatomy, and cause the GUI to display at least one indicium of the MOA.

13. The external device of claim 12, wherein the displayed indicium of the MOA reflects a preferential activation of a first neural fiber type compared to other neural fiber types.

14. The external device of claim 12, wherein the displayed indicium of the MOA reflects a presence or absence of paresthesia.

15. A non-transitory computer-readable medium for use with an external device for programming an implantable medical device (IMD) implantable in a patient, wherein the IMD comprises an implantable pulse generator (IPG) and one or more lead wires each comprising a plurality of electrodes, wherein the computer-readable medium comprises instructions which, when executed by a processor of the external device, configure the processor to:
render a graphical user interface (GUI) on a screen of the external device,
cause the GUI to display a representation of the patient's anatomy,
receive input from a user indicating at least a first stimulation waveform to be applied at a first one or more electrodes of the plurality of electrodes and a second stimulation waveform to be applied at a second one or more electrodes of the plurality of electrodes, and
cause the GUI to display at least one indicium of one or more interactions of the combined first and second stimulation waveforms with the patient's anatomy.

16. The non-transitory computer-readable medium of claim 15, wherein the indicium of one or more interactions indicates a constructive activation of neural elements within the patient's anatomy by the first and second waveforms.

17. The non-transitory computer-readable medium of claim 15, wherein the indicium of one or more interactions indicates a region of the patient's anatomy comprising neural elements not activated by the first or second waveforms because of destructive interaction with the first and second waveforms.

18. The non-transitory computer-readable medium of claim 15, wherein the indicium of one or more interactions indicates a first center point of stimulation (CPS) arising from the first stimulation waveform and a second CPS arising from the second stimulation waveform.

19. The non-transitory computer-readable medium of claim 15, wherein the processor is further configured to:
receive input from a user specifying a change of one or more of the first and second stimulation waveforms as a function of time, and
cause the GUI to display a time-resolved representation of a variance of the at least one indicium changes as a function of time.

20. The non-transitory computer-readable medium of claim 19, wherein the time-resolved representation of the variance of the at least one indicium reflects a constructive or destructive interaction of the first and second waveforms within the patient's anatomy.

* * * * *